(12) United States Patent
Dempsey

(10) Patent No.: US 11,931,486 B2
(45) Date of Patent: Mar. 19, 2024

(54) DIFFUSER

(71) Applicant: Dempsey Holdings, LLC, Argyle, TX (US)

(72) Inventor: Jake Dempsey, Argyle, TX (US)

(73) Assignee: DEMPSEY HOLDINGS, LLC, Argyle, TX (US)

( * ) Notice: Subject to any disclaimer, the term of this patent is extended or adjusted under 35 U.S.C. 154(b) by 0 days.

(21) Appl. No.: 17/579,374

(22) Filed: Jan. 19, 2022

(65) Prior Publication Data
US 2023/0226244 A1 Jul. 20, 2023

(51) Int. Cl.
*A61L 9/12* (2006.01)

(52) U.S. Cl.
CPC .............. *A61L 9/122* (2013.01); *A61L 9/125* (2013.01); *A61L 2209/11* (2013.01); *A61L 2209/133* (2013.01); *A61L 2209/134* (2013.01)

(58) Field of Classification Search
CPC . A61L 9/122; A61L 9/125; A61L 9/14; A61L 2209/11; A61L 2209/133; A61L 2209/134
See application file for complete search history.

(56) References Cited

U.S. PATENT DOCUMENTS

| | | | |
|---|---|---|---|
| 9,421,295 B1* | 8/2016 | Li | A61L 9/14 |
| 9,439,995 B2* | 9/2016 | Conroy | B05B 7/2416 |
| D881,366 S | 4/2020 | Kihm et al. | |
| D881,367 S | 4/2020 | Kihm et al. | |
| 11,000,618 B2* | 5/2021 | Lee | B05B 7/2491 |
| 11,052,356 B2* | 7/2021 | Ansley | B05B 7/265 |
| 2017/0360981 A1 | 12/2017 | Avidor | |
| 2018/0304296 A1 | 10/2018 | Tkachenko et al. | |
| 2018/0369847 A1 | 12/2018 | Kihm et al. | |
| 2018/0373272 A1 | 12/2018 | Kihm et al. | |
| 2019/0008992 A1 | 1/2019 | Kihm et al. | |
| 2020/0009284 A1 | 1/2020 | Kihm | |
| 2020/0330721 A1* | 10/2020 | Chang | A61L 9/122 |

* cited by examiner

*Primary Examiner* — Timothy C Cleveland
(74) *Attorney, Agent, or Firm* — HAYNES AND BOONE, LLP

(57) ABSTRACT

An essential oil diffuser including multiple diffuser channels. Each diffuser channel includes an air pump and a cartridge assembly. The cartridge assemblies are removable receivable within a chassis assembly of the diffuser.

8 Claims, 12 Drawing Sheets

DIFFUSER

TECHNICAL FIELD

This application is related generally to essential oil diffusers, and, more particularly, to a single-chassis assembly diffuser including multiple diffuser channels, each having its own air pump.

BACKGROUND

An essential oil diffuser is a device that takes a viscous liquid essential oil (such as peppermint) and works to atomize the particle of the essential oil into the air. Many devices exist for diffusing essential oils. These devices are typically of two varieties, namely ultrasonic diffusers and nebulizing diffusers. The first, which is the most common and least expensive type of diffuser, uses ultrasonic plate(s) to diffuse a mixture of water and essential oil. Specifically, an ultrasonic diffuser requires the user to place droplets of the essential oil into a water bath (typically distilled water) which is then vibrated by an ultrasonic plate and causes the water droplets to atomize; as the water droplets atomize, they also carry some of the essential oil into the air. The drawbacks of ultrasonic diffusers include, but are not limited to, the user having to deal with the water, cleaning the diffuser, potentially getting mold and mildew in the reservoir if not emptied, waste via throwing out the water when you want to diffuse a different essential oil, lack of variability in the diffusion (once the user puts the essential oil into the water bath, he/she can intensify the mixture by adding more oil, but cannot remove oil), etc.

The second, which is typically more expensive as it requires more parts and tighter tolerances, is a waterless nebulizing diffuser that diffuses a pure essential oil(s) using the Bernoulli Effect by directing fast-moving air above a siphon tube. Specifically, a nebulizing diffuser utilizes fast moving air across a siphon to create a low pressure zone that causes a reservoir of pure essential oil (with no water) to be drawn up the siphon. As the essential oil reaches the top of the siphon it hits the fast moving air, causing some of the essential oil to be atomized and released into the atmosphere. The un-atomized essential oil is thrown against the wall of the diffuser and returns back to the oil reservoir. This process allows for finer control of the essential oil being dispersed because the user can control the amount of essential oil that is atomized by controlling the velocity of the air moving across the siphon. Nebulizing diffusers are typically more expensive than ultrasonic diffusers because they work with much tighter tolerances to create the proper low pressure zone/vacuum and require an air pump to operate. The challenge with existing nebulizing diffusers is that they only allow for one essential oil reservoir.

Therefore, what is needed is an apparatus, system, method, or any combination thereof, to address one or more of the foregoing issues, and/or one or more other issues.

DETAILED DESCRIPTION

Figure 1A:
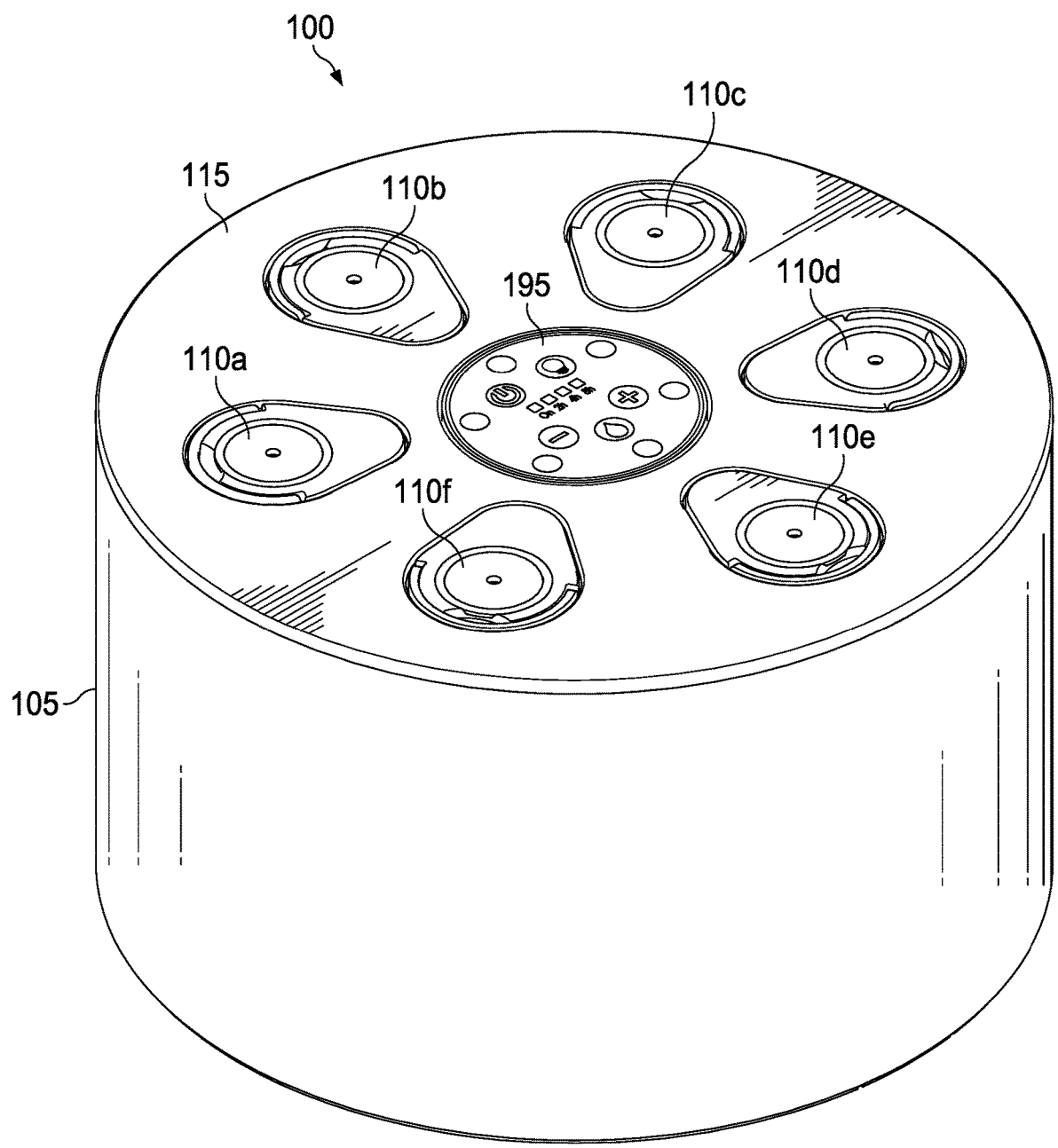
FIG. 1A is a perspective view of a diffuser, according to one or more embodiments of the present disclosure.
Figure 1B:
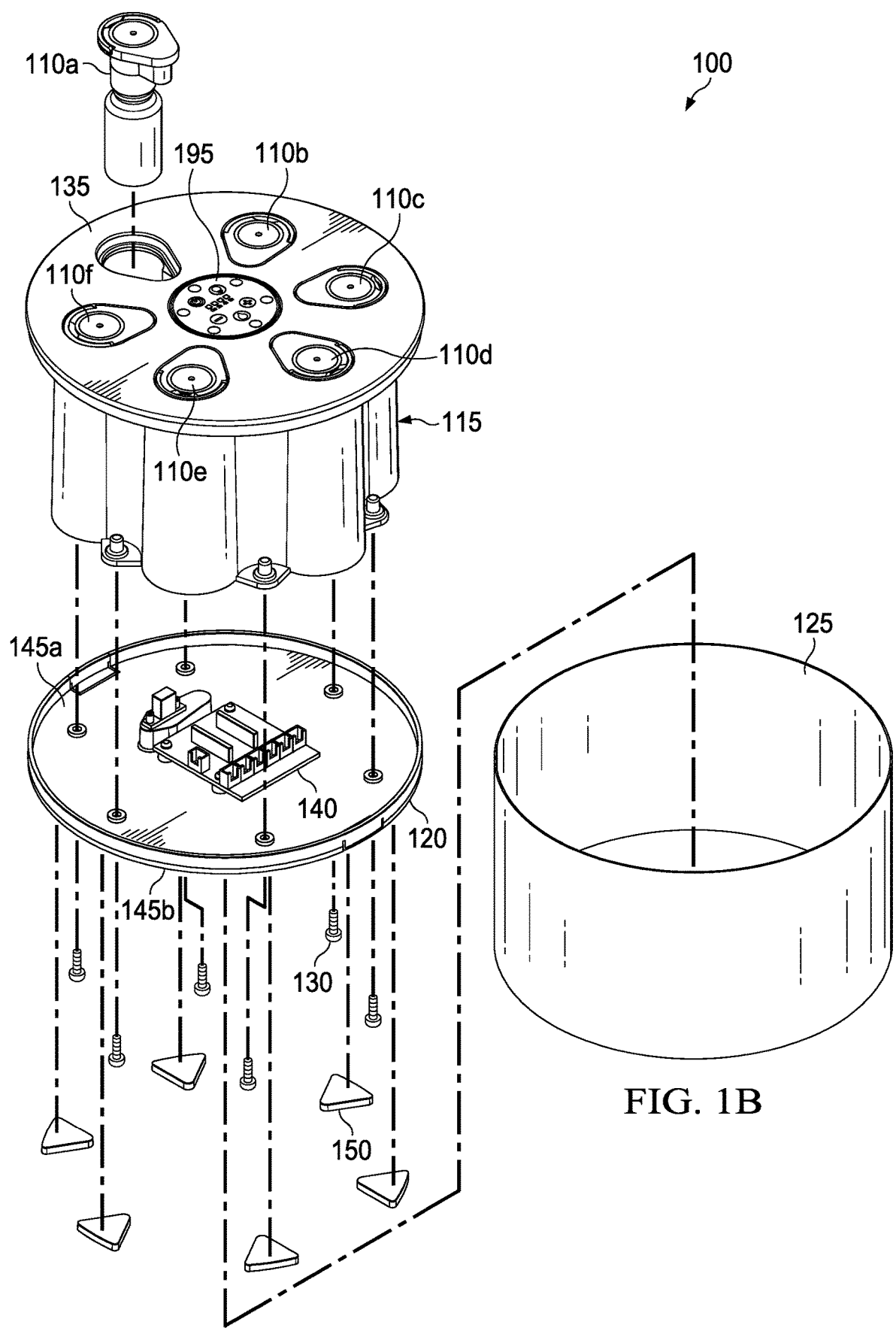
FIG. 1B is an exploded perspective view of the diffuser of FIG. 1A, according to one or more embodiments of the present disclosure.

Referring to FIGS. 1A and 1B, in an embodiment, a diffuser (e.g., a waterless diffuser) is generally referred to by the reference numeral 100. In one or more embodiments, the diffuser 100 allows a user to have up to six (6) bottles of essential oil(s) (e.g., one (1), two (2), three (3), four (4), five (5), or six (6) bottles of essential oil(s)) in a single chassis assembly 115 controlled by a controller 140 via a user interface 195 (either the device user interface 195 or a mobile app in communication with the controller 140 and or the device user interface 195). In other embodiment(s), the diffuser 100 allows a user to have more than (6) bottles of essential oil(s) (e.g., seven (7), eight (8), nine (9), ten (10), or more bottles of essential oil(s)) in the chassis assembly 115 controlled by the controller 140 via the user interface 195. Specifically, the diffuser 100 allows the user to run any one or more of the bottles at particular intensit(ies) (e.g., levels 1 to 10) to create a customized blend (e.g., by running multiple bottles at the same time at various intensities). In one or more embodiments, the diffuser 100 is or includes a nebulizing-type diffuser that provides a user with six (6) separate slots for essential oils, each of which is independently controllable to diffuse varying amounts of essential oil. In one or more embodiments, the diffuser 100 allows the user to provide his or her own essential oils, to run each slot independently (or together), and to utilize either the device controls or a mobile application to control the device. This encourages the sharing of diffuser recipes between users (for instance, it is common to diffuse a blend of lemon, lavender, and peppermint for allergies). The diffuser 100 enables the user to decide what intensity he or she wants for each oil individually, thereby permitting him or her to change the ratios of a blend on the fly, tweaking a recipe to his or her needs while using the essential oils he or she knows and trusts from the brand he or she is accustomed to purchasing from.

In one or more embodiments, the diffuser 100 has six (6) slots designed to take many commonly sized essential oil bottles on the market from various essential oil companies. For example, many essential oil companies utilize a DIN19 head on their bottles; accordingly, in one or more embodiments, the diffuser 100 accepts DIN19 bottle heads. For another example, the diffuser 100 includes the chassis assembly 115 from which varying sizes of bottles can be suspended (e.g., 5 ml, 10 ml, 15 ml, etc.). Once each of the six (6) bottles is inserted into the diffuser 100 with its corresponding diffuser cap 235 (see FIG. 3A), a seal is created to allow air flow from one of six (6) air pumps 160*a-f* to reach the diffuser cap 235. The controller 140 (which may have Wi-Fi capability) controls the diffuser 100 and allows the user (through the user interface 195 or a mobile application) to select a particular channel 420*a-f* of the diffuser 100 and adjust its intensity up or down (e.g., from 0 to 10). In this manner, the user can run just one (1) of the channels 420*a-f* or any combination of the six (6) channels 420*a-f* at varying intensities.

As shown in FIG. 1A, the diffuser 100 includes a main housing 105, cartridge assemblies 110*a-f*, and the chassis assembly 115. The chassis assembly 115 is received within, and connected to, the main housing 105. The cartridge assemblies 110*a-f* are each receivable within the chassis assembly 115. As shown in FIG. 1B, the main housing 105 includes a bottom cover 120 and an outer wall 125. The bottom cover 120 is connected to the chassis assembly 115 via fasteners 130. The outer wall 125 is contained between the bottom cover 120 and a top cover 135 of the chassis assembly 115. The controller 140 is connected to an inside 145*a* of the bottom cover 120. The bottom cover 120 includes an outside 145*b* to which feet 150 (e.g., anti-slip feet) are connected to support the diffuser 100.

Figure 2A:
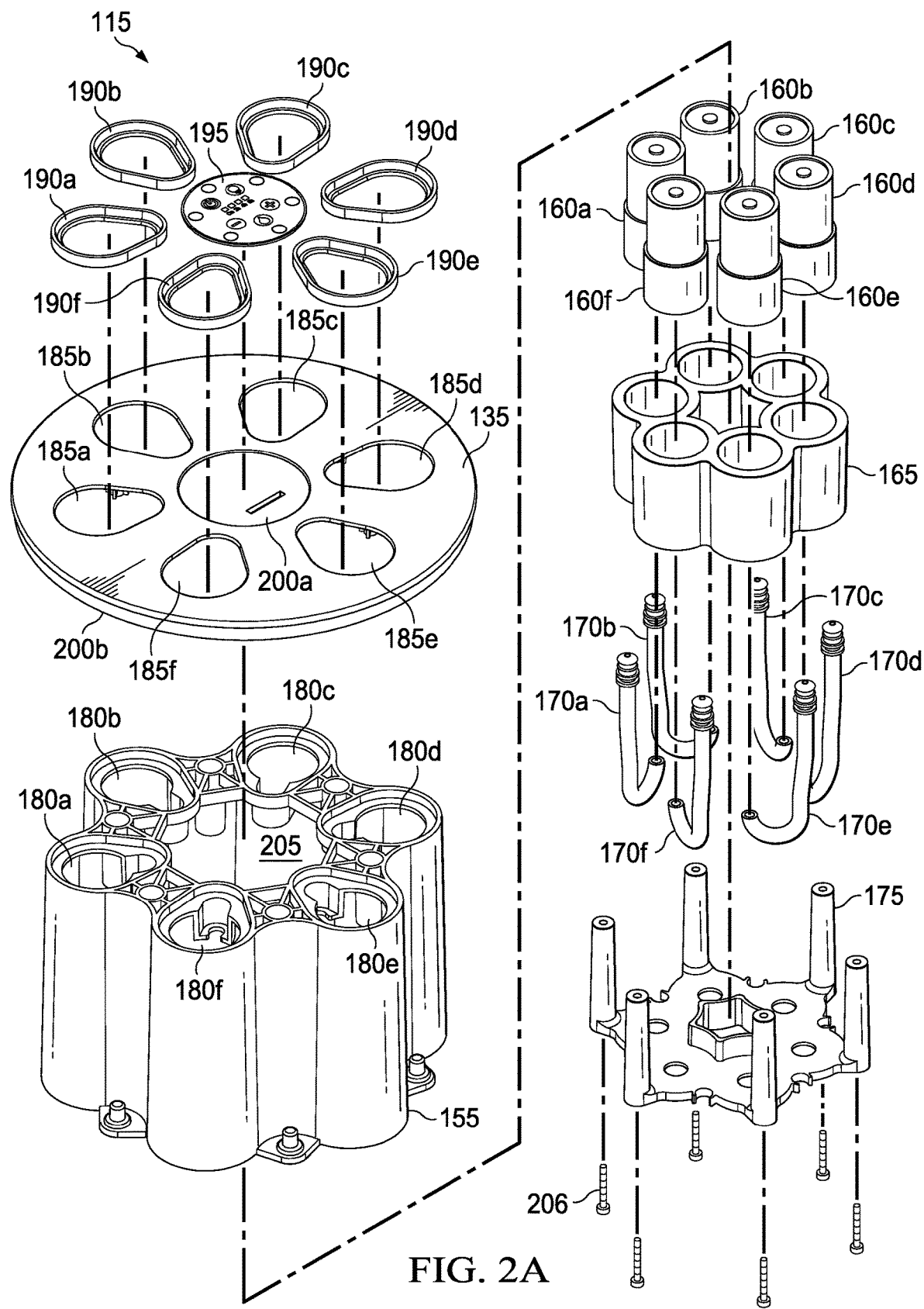
FIG. 2A is an exploded perspective view of a chassis assembly of the diffuser of FIGS. 1A and 1B, according to one or more embodiments.
Figure 2B:
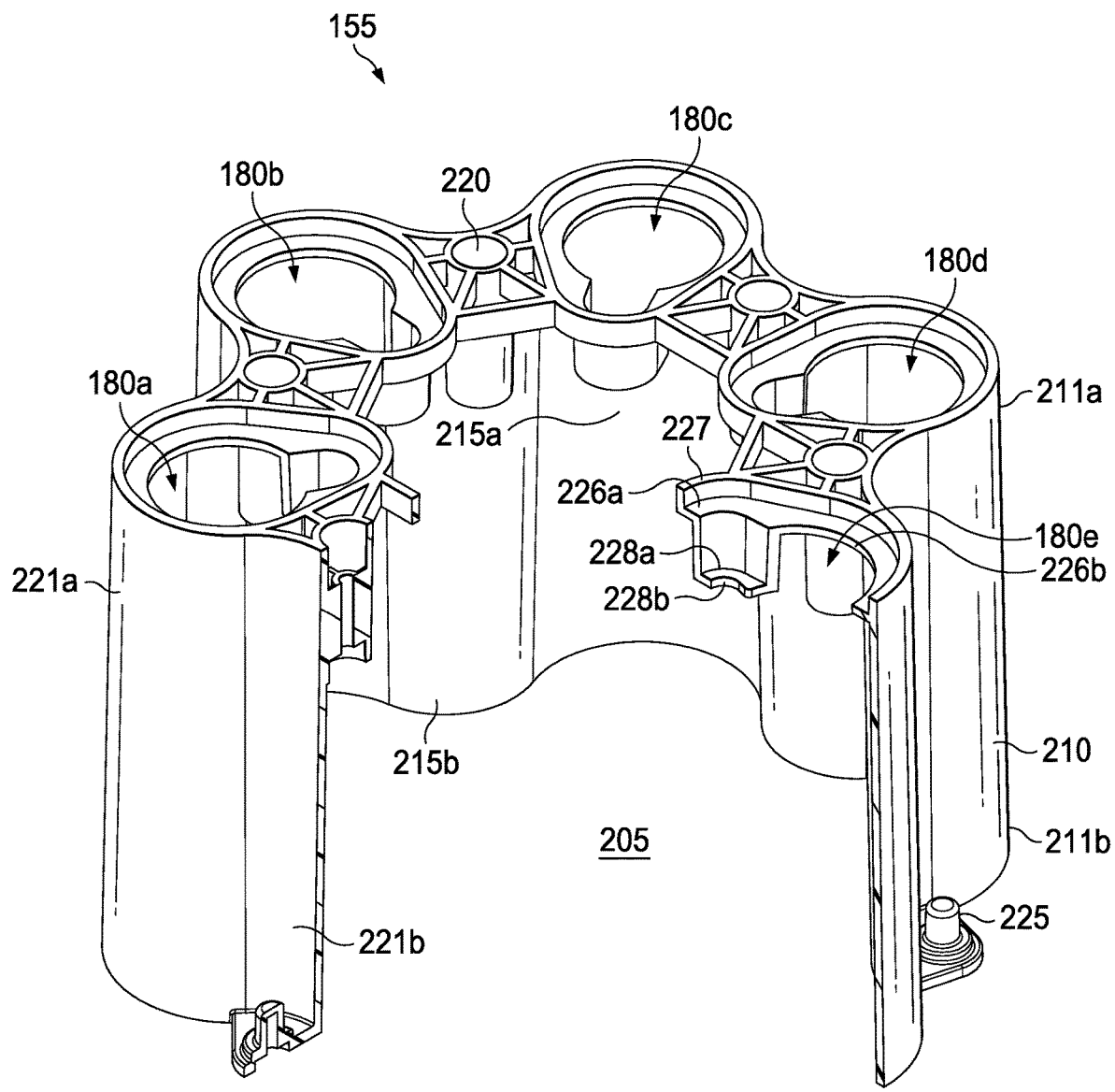
FIG. 2B is a perspective view of a cylinder of the chassis assembly of FIG. 2A in partial cross section, according to one or more embodiments.

Referring to FIGS. 2A and 2B, with continuing reference to FIGS. 1A and 1B, in an embodiment, the chassis assembly 115 includes the top cover 135, a cylinder 155, the air pumps 160*a-f*, an adapter 165, conduits 170*a-f*, and a cradle 175. As shown in FIG. 2A, the cylinder 155 includes receptacles 180*a-f*. The top cover 135 includes openings 185*a-f* aligned with the respective receptacles 180*a-f*. The openings 185*a-f* and the receptacles 180*a-f*, in respective combinations, receive the respective cartridge assemblies 110*a-f*. More particularly, the respective receptacles 180*a-f* receive respective pads 190*a-f* (e.g., sealing pads) to cushion (e.g., sealingly) the cylinder 155 against the respective cartridge assemblies 110*a-f*. The user interface 195 (also shown in FIGS. 1A and 1B) is connected to an outside 200*a* of the top cover 135. The user interface 195 communicates with the controller 140. In one or more embodiments, the user interface 195 is, includes, or is part of the controller 140. The cylinder 155 further includes an internal region 205 in which the air pumps 160*a-f* are contained. Specifically, the adapter 165 retains the respective air pumps 160*a-f* within the cradle 175, and fasteners 206 connect the cradle 175 and the cylinder 155 to an inside 200*b* of the top cover 135, thereby securing the air pumps 160*a-f* within the internal region 205. The conduits 170*a-f*, which extend through the adapter 165 (and the cradle 175), operably couple the respective air pumps 160*a-f* to the respective cartridge assemblies 110*a-f*.

As shown in FIG. 2B, the cylinder 155 includes an outer wall 210 extending circumferentially around the internal region 205 and defining opposing end portions 211*a* and 211*b*. The receptacles 180*a-f* are connected to, and circumferentially spaced (e.g. evenly) around, the outer wall 210 at the end portion 211*a*. The outer wall 210 undulates circumferentially so as to define inwardly concave portions 215*a* and inwardly convex portions 215*b* circumferentially interposed between the inwardly concave portions 215*a*. The inwardly concave portions 215*a* are aligned with the respective receptacles 180*a-f* so as to accommodate the respective cartridge assemblies 110*a-f*. Fittings 220 are connected to, and circumferentially spaced (e.g. evenly) around, the outer wall 210 at the end portion 211*a*. The fittings 220, which receive the respective fasteners 206 (shown in FIG. 2) therethrough, are interposed between the receptacles 180*a-f* and aligned with the respective inwardly convex portions 215*b*. The outer wall 210 also defines outwardly convex portions 221*a* (located radially opposite the inwardly concave portions 215*a*) and outwardly concave portions 221*b* (located radially opposite the inwardly convex portions 215*b*) circumferentially interposed between the outwardly convex portions 221*a*. Fittings 225 are connected to, and circumferentially spaced (e.g., evenly) around, the outer wall 210 at the end portion 211*b*. The fittings 225, which receive the respective fasteners 130 (shown in FIG. 1B), are aligned with the respective outwardly concave portions 221*b*.

The receptacles 180*a-f* are substantially identical to one another, and, therefore, in connection with FIG. 3, only the receptacle 180*e* will be described in detail below; however, the description below applies equally to the receptacles 180*a-d* and 180*f*. As shown in FIG. 3, the receptacle 180*e* includes an upwardly-facing shoulder 226*a* extending circumferentially around an opening 226*b* and recessed from a top surface 227 of the cylinder 155. The shoulder 226*a* of the receptacle 180*e* receives the pad 190*e* to cushion against the cartridge assembly 110*e* (shown in FIGS. 1A and 1B) while the opening 226*b* receives a portion of the cartridge assembly 110*e* therethrough. The receptacle 180*e* also includes an upwardly-facing shoulder 228*a* extending partially around a slot 228*b* and recessed from the shoulder 226*a*. The shoulder 228*a* and the slot 228*b* of the receptacle 180*e* extend adjacent the opening 226*b* to retain the conduit 170*e*, as will be described in more detail below.

Figure 3A:
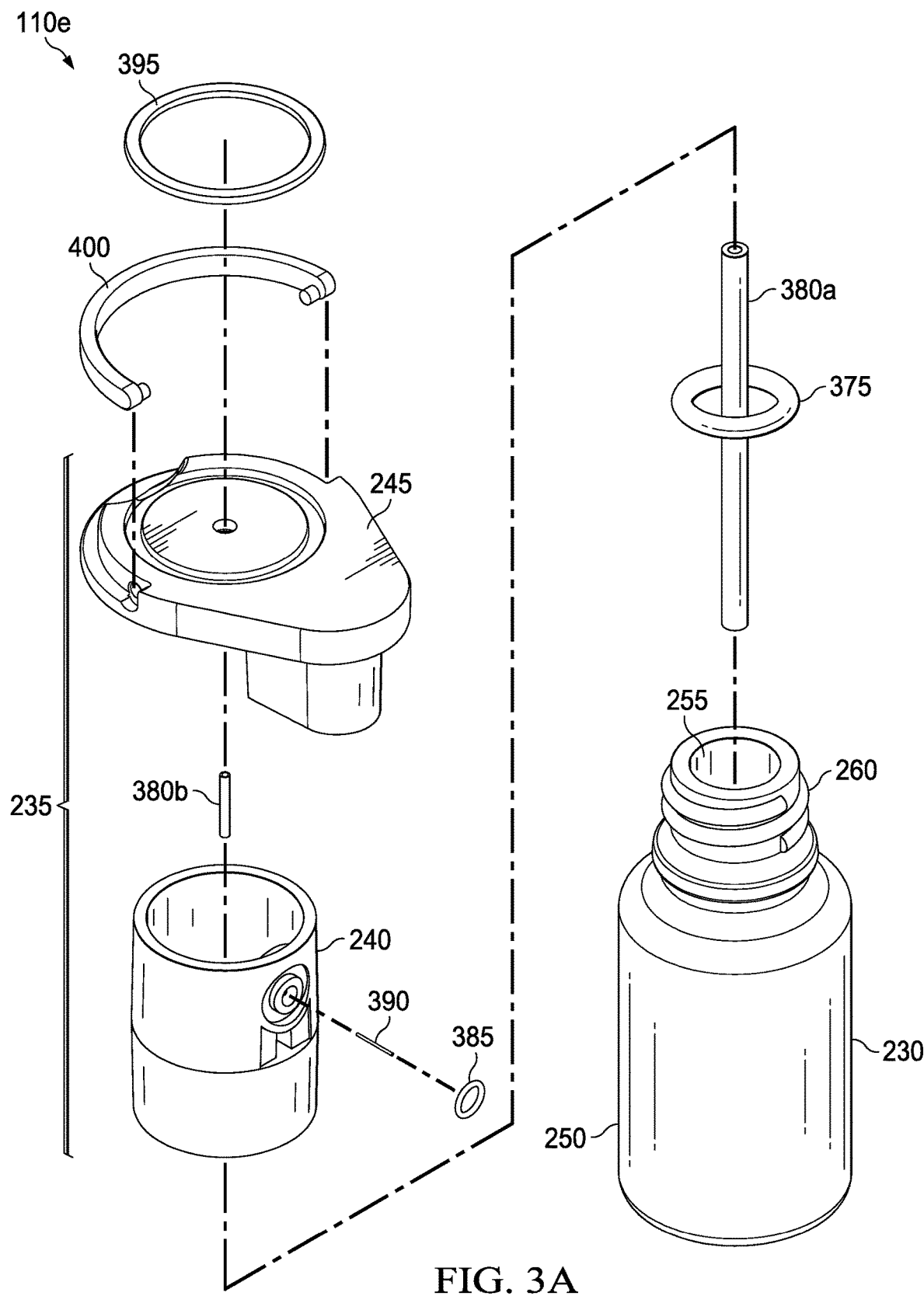
FIG. 3A is an exploded perspective view of a cartridge assembly of the diffuser of FIGS. 1A and 1B, according to one or more embodiments.

Referring to FIGS. 3A through 3D, with continuing reference to FIGS. 1A and 1B, the cartridge assembly 110*e* is illustrated according to one or more embodiments. The cartridge assemblies 110*a-f* are substantially identical to one another, and, therefore, in connection with FIGS. 3A through 3D, only the cartridge assembly 110*e* will be described in detail below; however the description below applies equally to the cartridge assemblies 110*a-d* and 110*f*. As shown in FIG. 3A, the cartridge assembly 110*e* includes a container 230 and the diffuser cap 235. The diffuser cap 235 includes a diffuser body 240 and a diffuser head 245. The container 230 includes a container body 250 and a container mouth 255. An external threaded connection 260 surrounds the container mouth 255.

Figure 3B:
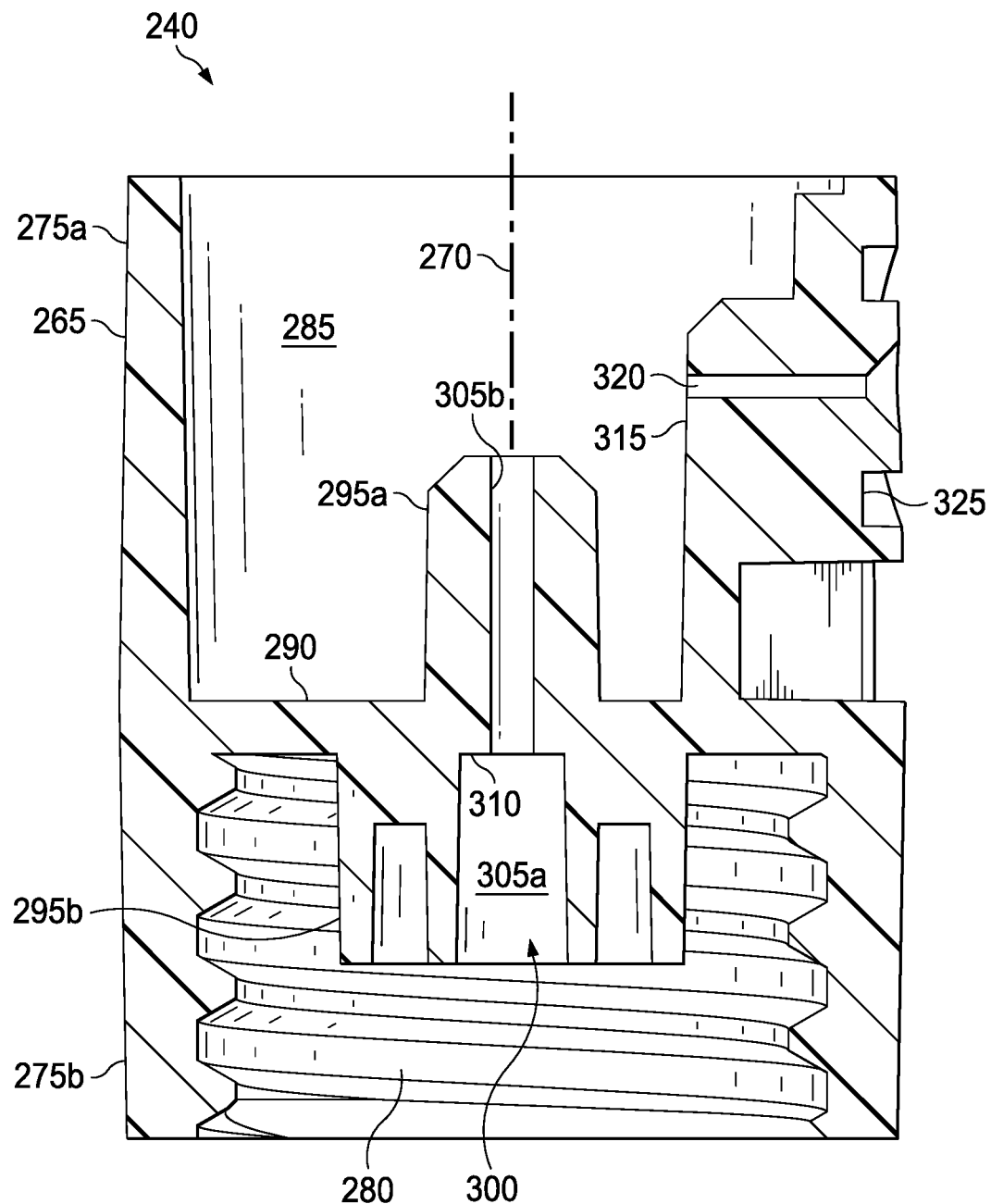
FIG. 3B is cross-sectional view of a diffuser body of a diffuser cap of the cartridge assembly of FIG. 3A, according to one or more embodiments.
Figure 3C:
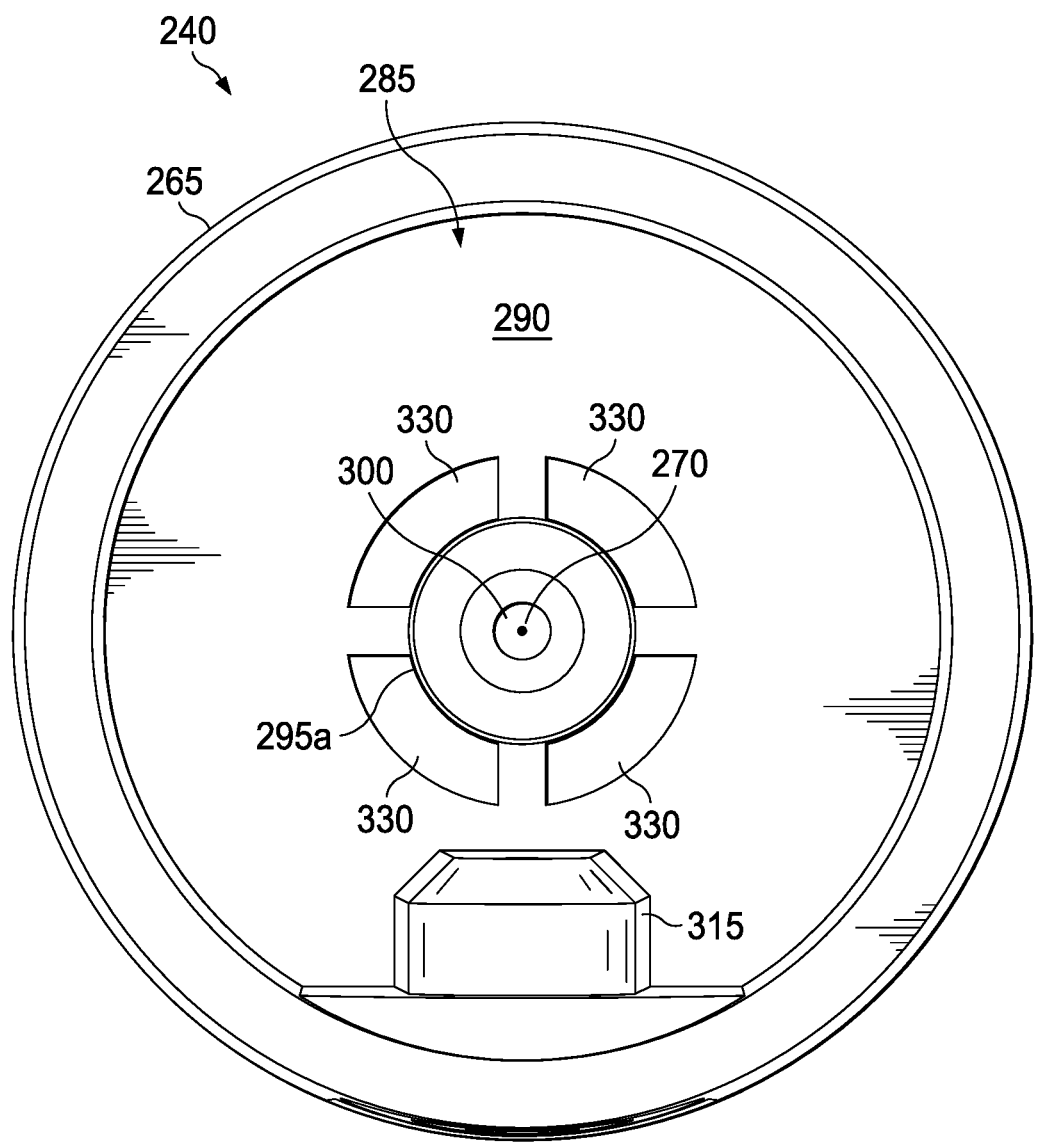
FIG. 3C is a top plan view of the diffuser body of FIG. 3B, according to one or more embodiments.

As shown in FIGS. 3B and 3C, the diffuser body 240 includes an outer wall 265 extending along an axis 270 and defining opposing end portions 275*a* and 275*b*. An internal threaded connection 280 is formed into the outer wall 265 at the end portion 275*b*. The internal threaded connection 280 connects the diffuser body 240 to the external threaded connection 260 of the container 230. The outer wall 265 surrounds an internal diffuser chamber 285 at the end portion 275*a*. An internal wall 290 separates the internal diffuser chamber 285 from the internal threaded connection 280. An internal protrusion 295*a* extends axially from the internal wall 290 into the internal diffuser chamber 285. Similarly, an internal protrusion 295*b* extends axially from the internal wall 290, opposite the internal protrusion 295*a*. An internal passageway 300 extends axially through the internal wall 290 and the internal protrusions 295*a-b*. The internal passageway 300 defines an enlarged-diameter portion 305*a* and a reduced-diameter portion 305*b*. The enlarged-diameter portion 305*a* defines a downwardly-facing internal shoulder 310 in the diffuser body 240, adjacent the reduced-diameter portion 305*b*. An internal protrusion 315 extends radially from the outer wall 265 into the internal diffuser chamber 285. An internal passageway 320 extends radially through the outer wall 265 and the internal protrusion 315. An external sealing groove 325 is formed radially into the outer wall 265, around the internal passageway 320. Openings 330 are formed axially through the internal wall 290 from the internal diffuser chamber 285, as shown in FIG. 3C. The openings 330 are circumferentially spaced around the internal protrusion 295a.

Figure 3D:
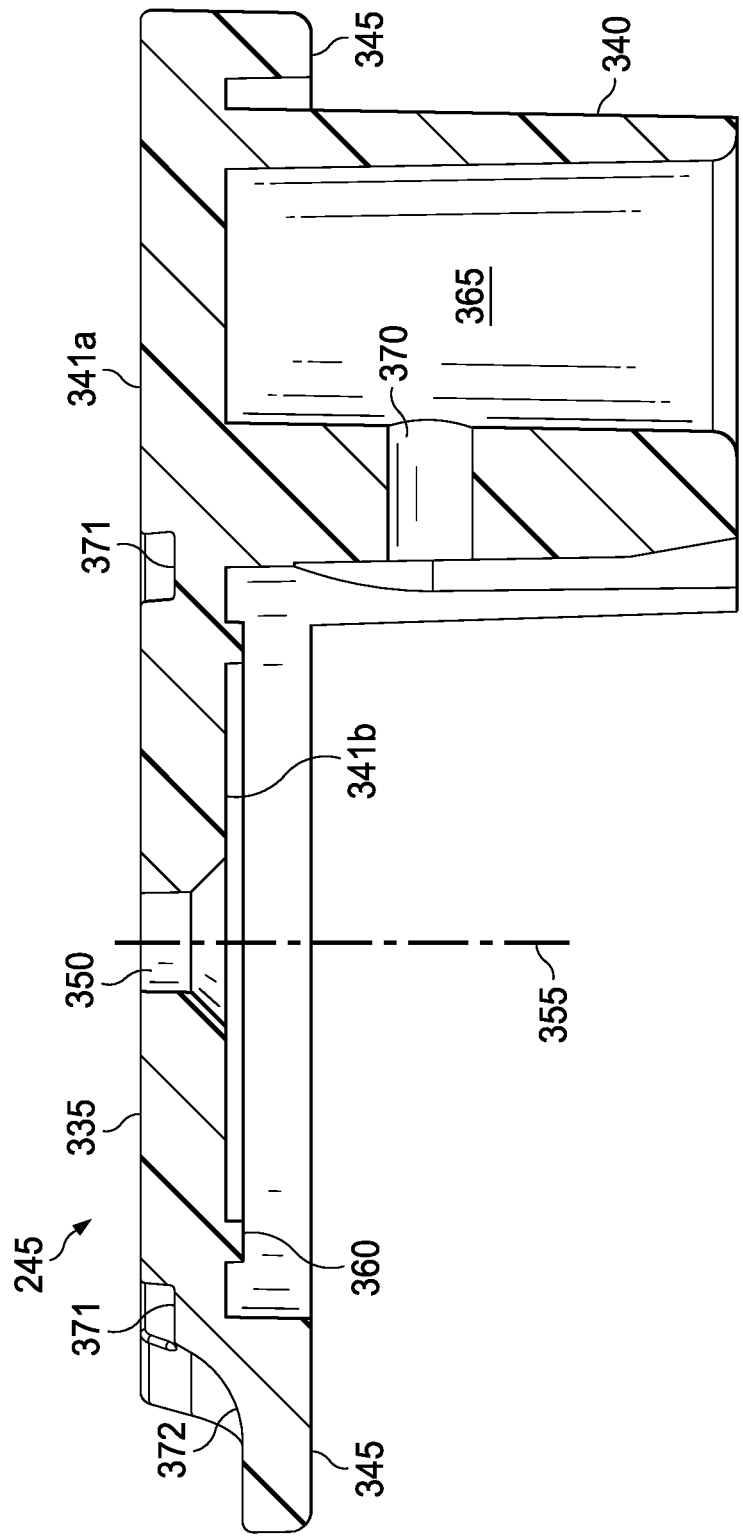
FIG. 3D is a cross-sectional view of a diffuser head of the diffuser cap of the cartridge assembly of FIG. 3A, according to one or more embodiments.

As shown in FIG. 3D, the diffuser head 245 includes a cover 335 and a pressure connection 340. The cover defines opposing top and bottom side portions 341a and 341b. An outer lip 345 of the cover 335 is engaged (e.g., sealingly) by the pad 190e, which pad 190e also engages (e.g., sealingly) the shoulder 226a of the receptacle 180e. The outer lip 345 extends downwardly from the side portion 341b. An opening 350 is formed through the cover 335 along an axis 355. An annular ridge 360 extends downwardly from the cover 335 along the axis 355. The annular ridge 360 is engaged by the outer wall 265 of the diffuser body 240 at the end portion 275a, thereby aligning the diffuser body 240 with the diffuser head 245. The pressure connection 340 extends downwardly from the cover 335, next to the annular ridge 360, and engages the conduit 170e, which conduit 170e is retained within the slot 228b of the receptacle 180e by the shoulder 228a. The pressure connection 340 defines an internal pressure chamber 365. An internal passageway 370 extends radially inwardly through the pressure connection 340 from the internal pressure chamber 365. The internal passageway 370 of the diffuser head 245 is aligned with the internal passageway 320 of the diffuser body 240 when the annular ridge 360 is engaged by the outer wall 265 of the diffuser body 240 at the end portion 275a. An annular groove 371 is formed into the side portion 341a of the cover 335 along the axis 355. A peripheral recess 372 is also formed into the side portion 341a of the cover 335, opposite the pressure connection 340, extending circumferentially part-way around the cover 335.

Turning back again to FIG. 3A, with continuing reference to FIGS. 3B through 3D, in an embodiment, the cartridge assembly 110e also includes a seal 375, an enlarged-diameter siphon tube 380a, a reduced-diameter siphon tube 380b, a seal 385, an atomizer tube 390, an annular inlay 395, and a handle 400. The seal 375 (e.g., an O-ring) is sealingly engaged between the container 230 and the internal wall 290 of the diffuser body 240, opposite the diffuser chamber 285. The enlarged-diameter siphon tube 380a is received within the enlarged-diameter portion 305a of the internal passageway 300 and into engagement with the internal shoulder 310 of the diffuser body 240. The enlarged-diameter siphon tube 380a also extends through the container mouth 255 and into the container body 250 of the container 230. The reduced-diameter siphon tube 380b is received within the reduced-diameter portion 305b of the internal passageway 300 and into engagement with the diffuser body 240. The reduced-diameter siphon tube 380b also extends into the diffuser chamber 285 of the diffuser body 240. The seal 385 (e.g., an O-ring) is received within the external sealing groove 385 of the diffuser body 240. The seal 385 is also sealingly engaged between the diffuser body 240 and the pressure connection 340 of the diffuser head 245. The atomizer tube 390 is received within the internal passageway 320 and into engagement with the diffuser body 240. The atomizer tube 390 also extends into the diffuser chamber 285 of the diffuser body 240, proximate the reduced-diameter siphon tube 380b. The annular inlay 395 is received within the annular groove 371 of the diffuser head 345. The handle 400 is pivotably connected to the diffuser head 345 and receivable within the peripheral recess 372.

Figure 4A:
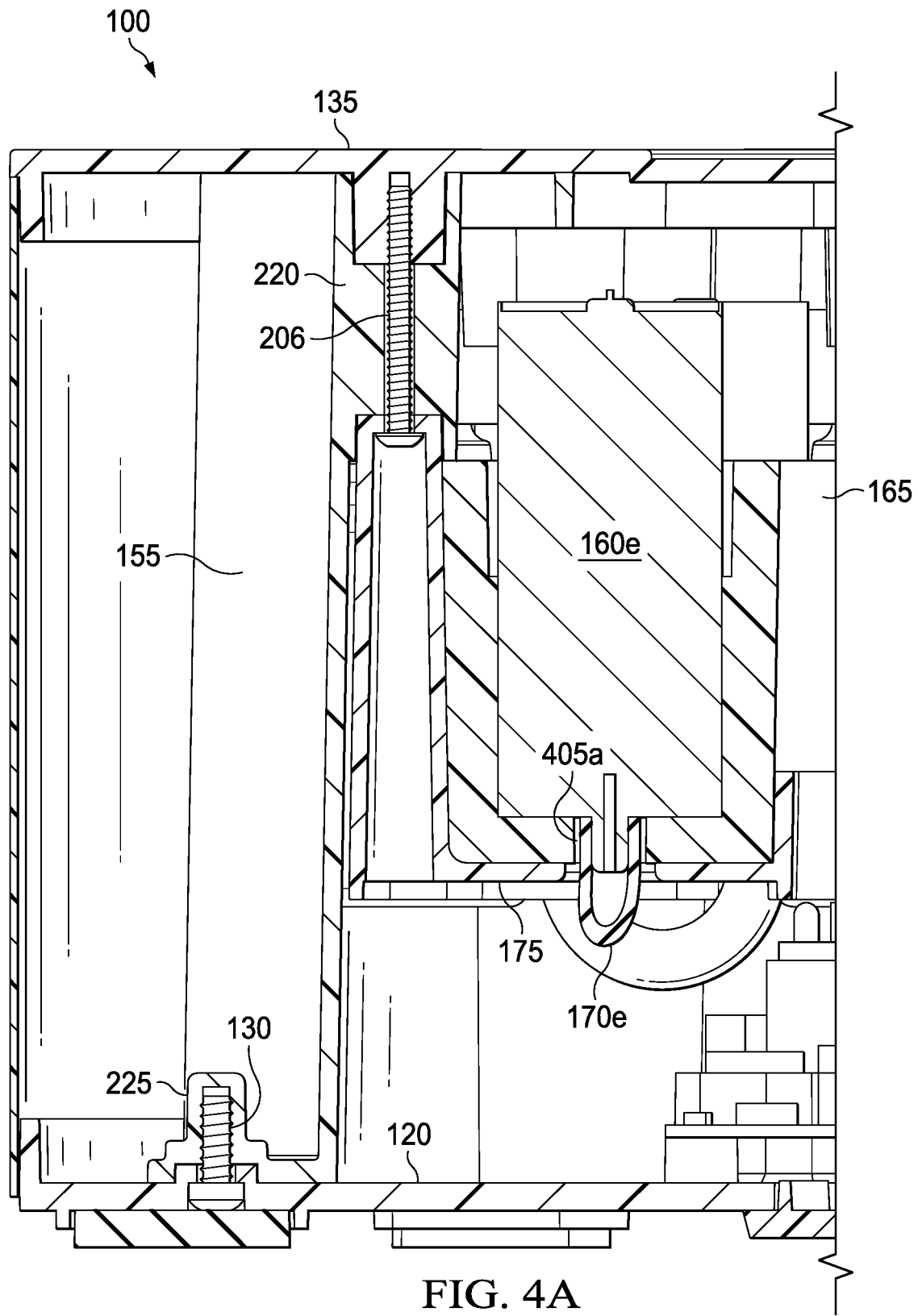
FIG. 4A is a cross-sectional view of the diffuser of FIG. 1A, according to one or more embodiments.
Figure 4B:
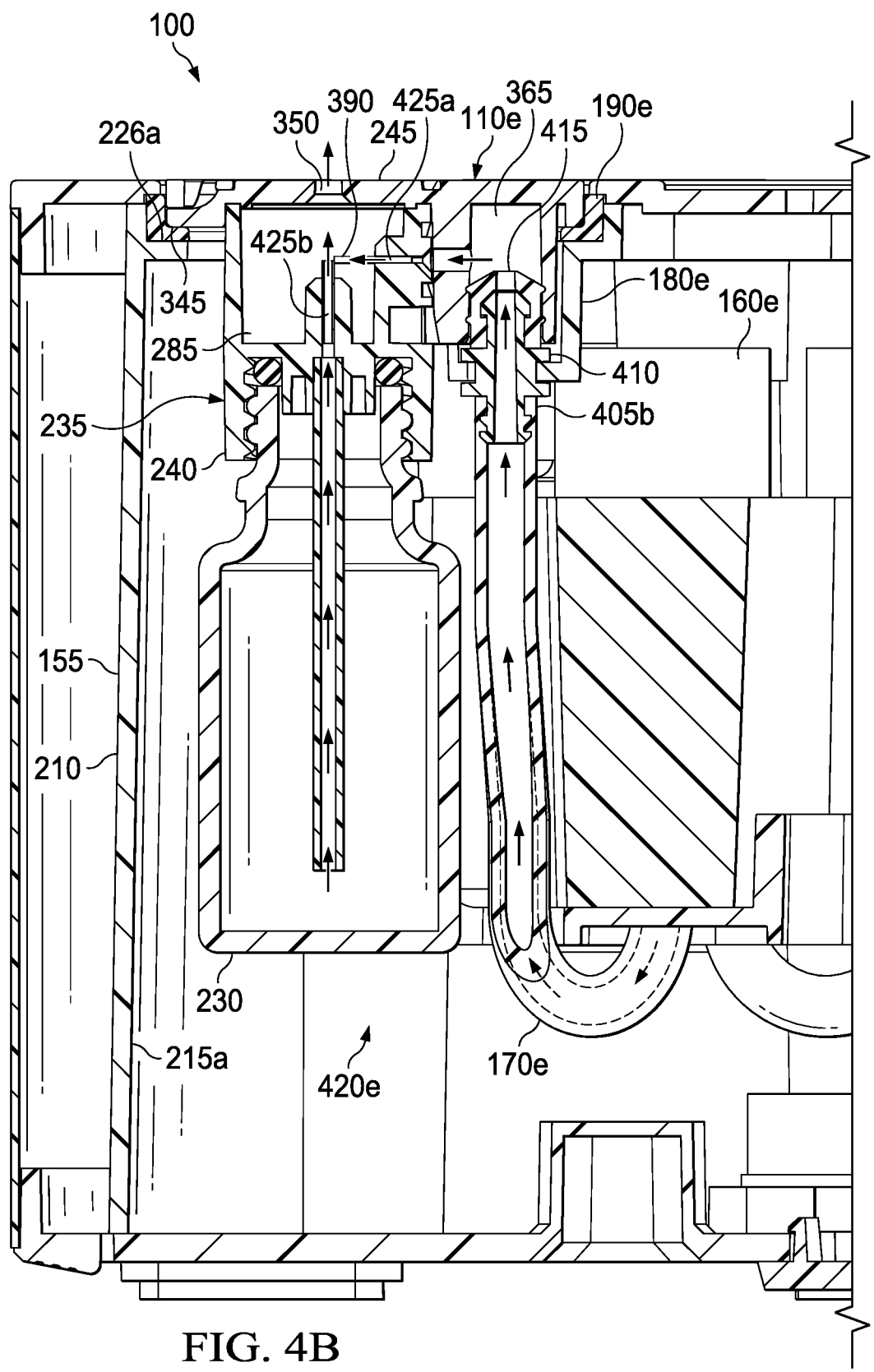
FIG. 4B is another cross-sectional view of the diffuser of FIG. 1A, according to one or more embodiments.

Referring to FIGS. 4A and 4B, with continuing reference to FIGS. 1A through 3D, the diffuser 100 is illustrated in an assembled state according to one or more embodiments. As shown in FIG. 4A, each of the fasteners 206 extends through the corresponding fitting 220 of the cylinder 155 to connect the cradle 175 (and the cylinder 155) to the top cover 135. Likewise, each of the fasteners 130 connects the bottom cover 120 to the corresponding fitting 225 of the cylinder 155. The air pump 160e is retained within the cradle 175 by the adapter 165. An end portion 405a of the conduit 170e is connected to the air pump 160e and extends through the adapter 165 (and the cradle 175). As shown in FIG. 4B, the conduit 170e also includes an end portion 405b, opposite the end portion 405a, and a fitting 410 located at the end portion 405b. The fitting 410 is retained within the slot 228b of the receptacle 180e by the shoulder 228a. The fitting 410 retains a seal 415, which seal 415 is received within the internal pressure chamber 365 to sealingly engage the diffuser head 245. The diffuser head 245 of the cartridge assembly 110e is supported (at the outer lip 345) on the shoulder 226a of the receptacle 180e by the pad 190e. As a result, the diffuser cap 235 suspends the container 230 within the internal region 205 of the cylinder 155, proximate the corresponding inwardly concave portion 215a of the outer wall 210.

In operation, the air pump 160e provides pressurized air to the pressure chamber 365 of the cartridge assembly 110e via the conduit 170e. The atomizer tube 390 and the internal passageways 320 and 370, in combination, form a flow path 425a via which the pressurized air flows from the pressure chamber 365 into the diffuser chamber 285. Likewise, the internal passageway 300 and the siphon tubes 380a and 380b, in combination, form a flow path 425b via which liquid (e.g., essential oil) flows from the container body 250 into the diffuser chamber 285. More particularly, a high-velocity stream of air exiting the flow path 425a intersects the flow path 425b in the diffuser chamber 285, creating a siphon effect that draws liquid from the container body 230 into the diffuser chamber 285 via the flow path 425b. The high-velocity stream of air exiting the flow path 425a atomizes at least a portion of the liquid exiting the flow path 425b. The atomized portion then exits the diffuser chamber 285 to atmosphere via the opening 350 in the diffuser head 245. The un-atomized portion of the liquid (if any) re-enters the container body via the openings 330 in the diffuser body 240.

The cartridge assembly 110e, the air pump 160e, the conduit 170e, and the receptacle 180e, in combination, form the channel 420e of the diffuser 100. Similarly, respective combinations of the cartridge assemblies 110a-d and 110f, the air pumps 160a-d and 160f, the conduits 170a-d and 170f, and the receptacles 180a-d and 180f form the respective channels 420a-d ad 420f of the diffuser 100; these channels 420a-d and 420f are assembled substantially identically (and include substantially identical features) to the channel 420e discussed above, and, therefore, will not be described in further detail. Additionally, the operation of the channels 420a-d and 420f are each substantially identical to the operation of the channel 420e, and, therefore, will not be described in further detail.

Figure 5:
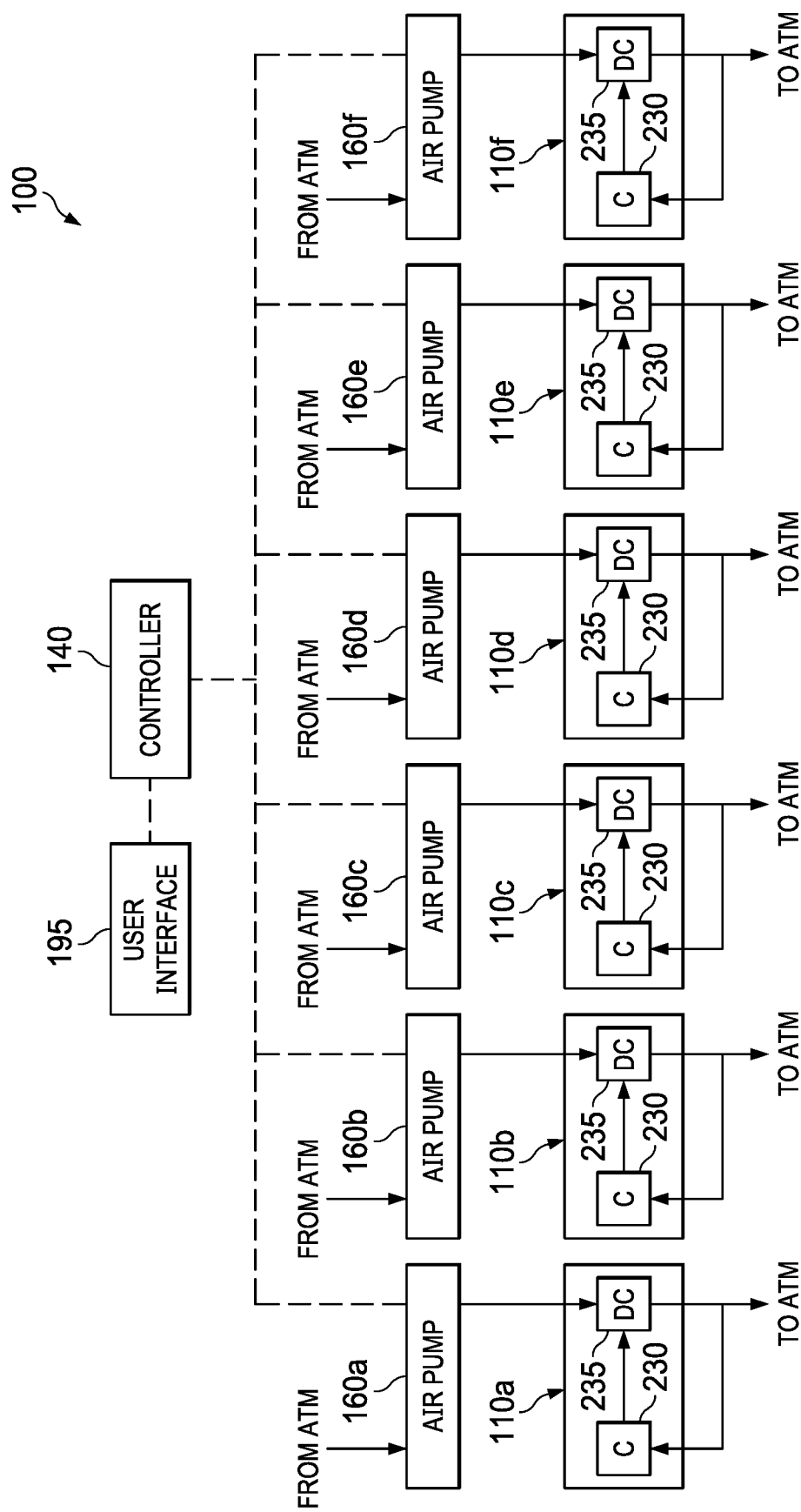
FIG. 5 is a diagrammatic illustration of the diffuser of FIGS. 1A and 1B, according to one or more embodiments.

Referring to FIG. 5, with continuing reference to FIGS. 1A through 4B, in an embodiment, the controller 140 communicates control signals to the air pumps 160a-f, which air pumps 160a-f are independently controllable by the control signals to diffuse varying amounts of the essential oils contained in the cartridge assemblies 110a-f, respectively. Specifically, the control signals communicates by the controller 140 may cause the air pumps 160*a-f* to supply air at varying speeds to the cartridge assemblies 110*a-f*, respectively. Thus, the diffuser 100 allows the user to run any one or more of the bottles at particular intensit(ies) (e.g., levels 1 to 10) to create a customized blend (e.g., by running multiple bottles at the same time at various intensities).

Figure 6:
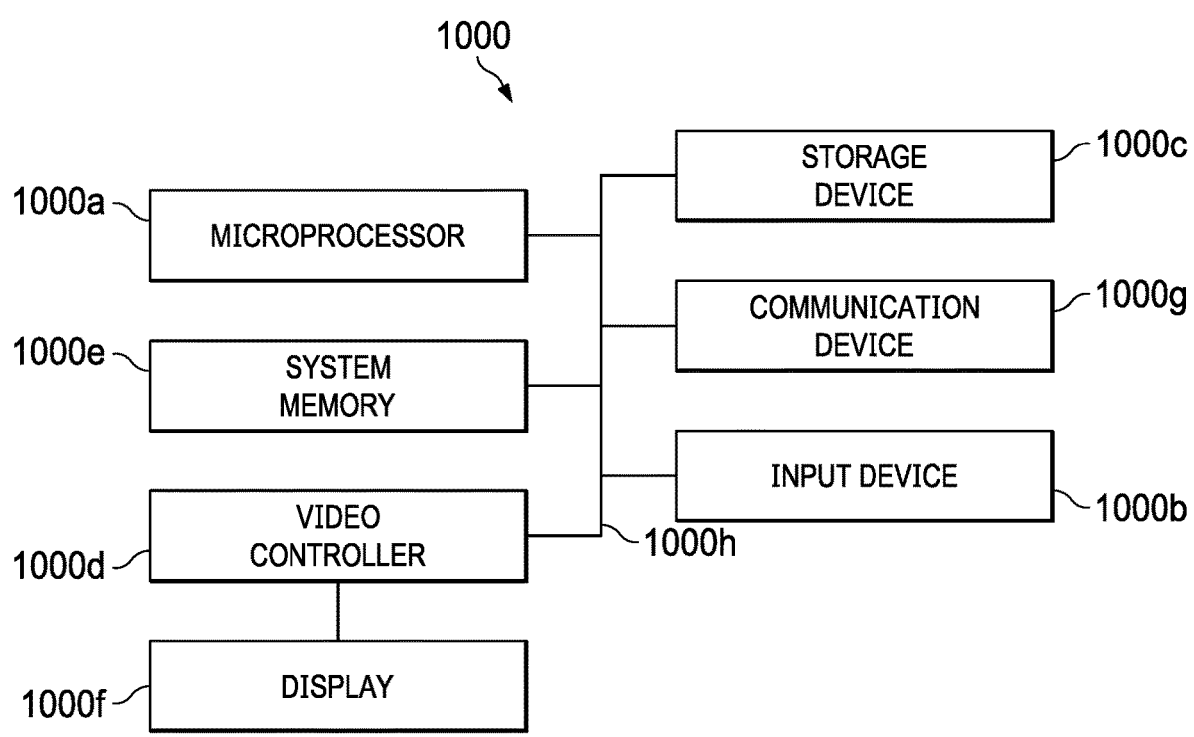
FIG. 6 is a diagrammatic illustration of a computing node for implementing one or more embodiments of the present disclosure.

Referring to FIG. 6, with continuing reference to FIGS. 1A through 5, an illustrative node 1000 for implementing embodiment(s) of one or more of the control unit(s), controller(s) (e.g., the controller 140), element(s), apparatus, system(s), method(s), step(s), or any combination thereof, described above and/or illustrated in FIGS. 1A through 5, is depicted. The node 1000 includes a microprocessor 1000*a*, an input device 1000*b*, a storage device 1000*c*, a video controller 1000*d*, a system memory 1000*e*, a display 1000*f*, and a communication device 1000*g* all interconnected by one or more buses 1000*h*. In one or more embodiments, the storage device 1000*c* may include a hard drive, CD-ROM, optical drive, any other form of storage device and/or any combination thereof. In one or more embodiments, the storage device 1000*c* may include, and/or be capable of receiving, a CD-ROM, DVD-ROM, or any other form of non-transitory computer-readable medium that may contain executable instructions. In one or more embodiments, the communication device 1000*g* may include a modem, network card, or any other device to enable the node 1000 to communicate with other node(s). In one or more embodiments, the node and the other node(s) represent a plurality of interconnected (whether by intranet or Internet) computer systems, including without limitation, personal computers, mainframes, PDAs, smartphones and cell phones.

In some implementations, one or more of the embodiments described above and/or illustrated in FIGS. 1A through 5 include at least the node 1000 and/or components thereof, and/or one or more nodes that are substantially similar to the node 1000 and/or components thereof. In some implementations, one or more of the above-described components of the node 1000 and/or the embodiments described above and/or illustrated in FIGS. 1A through 5 include respective pluralities of same components.

In some implementations, one or more of the embodiments described above and/or illustrated in FIGS. 1A through 5 include a computer program that includes a plurality of instructions, data, and/or any combination thereof; an application written in, for example, Arena, HyperText Markup Language (HTML), Cascading Style Sheets (CSS), JavaScript, Extensible Markup Language (XML), asynchronous JavaScript and XML (Ajax), and/or any combination thereof; a web-based application written in, for example, Java or Adobe Flex, which in one or more embodiments pulls real-time information from one or more servers, automatically refreshing with latest information at a predetermined time increment; or any combination thereof.

In one or more embodiments, a computer system typically includes at least hardware capable of executing machine readable instructions, as well as the software for executing acts (typically machine-readable instructions) that produce a desired result. In one or more embodiments, a computer system may include hybrids of hardware and software, as well as computer sub-systems.

In one or more embodiments, hardware generally includes at least processor-capable platforms, such as client-machines (also known as personal computers or servers), and hand-held processing devices (such as smart phones, tablet computers, or personal computing devices (PCDs), for example). In one or more embodiments, hardware may include any physical device that is capable of storing machine-readable instructions, such as memory or other data storage devices. In one or more embodiments, other forms of hardware include hardware sub-systems, including transfer devices such as modems, modem cards, ports, and port cards, for example.

In one or more embodiments, software includes any machine code stored in any memory medium, such as RAM or ROM, and machine code stored on other devices (such as floppy disks, flash memory, or a CD-ROM, for example). In one or more embodiments, software may include source or object code. In one or more embodiments, software encompasses any set of instructions capable of being executed on a node such as, for example, on a client machine or server.

In one or more embodiments, combinations of software and hardware could also be used for providing enhanced functionality and performance for certain embodiments of the present disclosure. In an embodiment, software functions may be directly manufactured into a silicon chip. Accordingly, it should be understood that combinations of hardware and software are also included within the definition of a computer system and are thus envisioned by the present disclosure as possible equivalent structures and equivalent methods.

In one or more embodiments, computer readable media include, for example, passive data storage, such as a random-access memory (RAM) as well as semi-permanent data storage such as a compact disk read only memory (CD-ROM). One or more embodiments of the present disclosure may be embodied in the RAM of a computer to transform a standard computer into a new specific computing machine. In one or more embodiments, data structures are defined organizations of data that may enable an embodiment of the present disclosure. In an embodiment, a data structure may provide an organization of data, or an organization of executable code.

In one or more embodiments, any networks and/or one or more portions thereof may be designed to work on any specific architecture. In an embodiment, one or more portions of any networks may be executed on a single computer, local area networks, client-server networks, wide area networks, internets, hand-held and other portable and wireless devices and networks.

In one or more embodiments, a database may be any standard or proprietary database software. In one or more embodiments, the database may have fields, records, data, and other database elements that may be associated through database specific software. In one or more embodiments, data may be mapped. In one or more embodiments, mapping is the process of associating one data entry with another data entry. In an embodiment, the data contained in the location of a character file can be mapped to a field in a second table. In one or more embodiments, the physical location of the database is not limiting, and the database may be distributed. In an embodiment, the database may exist remotely from the server, and run on a separate platform. In an embodiment, the database may be accessible across the Internet. In one or more embodiments, more than one database may be implemented.

In one or more embodiments, one or more of the above-described methods are executed, at least in part, using a proportional-integral-derivative (PID) control system, a PID controller, other type(s) of control systems, other type(s) of controllers, or any combination thereof. In one or more embodiments, the controller 140 is, includes, or is part of, a PID controller, a PID control system, other type(s) of controllers, or any combination thereof.

In one or more embodiments, a plurality of instructions stored on a non-transitory computer readable medium may be executed by one or more processors to cause the one or more processors to carry out or implement in whole or in part embodiment(s) of one or more of the control unit(s), controller(s) (e.g., the controller 140), element(s), apparatus, system(s), method(s), step(s), or any combination thereof, described above and/or illustrated in FIGS. 1A through 5. In one or more embodiments, such a processor may include one or more of the microprocessor 1000a, any processor(s) that are part of the components of the diffuser 100 (e.g., the controller 140), and/or any combination thereof, and such a computer readable medium may be distributed among one or more components. In one or more embodiments, such a processor may execute the plurality of instructions in connection with a virtual computer system. In one or more embodiments, such a plurality of instructions may communicate directly with the one or more processors, and/or may interact with one or more operating systems, middleware, firmware, other applications, and/or any combination thereof, to cause the one or more processors to execute the instructions.

A method has been disclosed. The method generally includes: supplying, using a first air pump of a diffuser, first pressurized air at a first pressure to a first cartridge assembly of the diffuser, said first cartridge assembly being removably received within a first receptacle of a chassis assembly of the diffuser; diffusing, with the first pressurized air supplied by the first air pump, a first liquid contained in the first cartridge assembly; supplying, using a second air pump of the diffuser, second pressurized air at a second pressure to a second cartridge assembly of the diffuser, said second cartridge assembly being removably received within a second receptacle of the chassis assembly of the diffuser; and diffusing, with the second pressurized air supplied by the second air pump, a second liquid contained in the second cartridge assembly. In one or more embodiments, the first pressure at which the first pressurized air is supplied to the first cartridge assembly of the diffuser by the first air pump is different from the second pressure at which the second pressurized air is supplied to the second cartridge assembly of the diffuser by the second air pump. In one or more embodiments, the method further includes: receiving, from a controller, first and second control signals at the first and second air pumps, respectively; wherein the first air pump supplies the first pressurized air at the first pressure to the first cartridge assembly in response to receiving the first control signal from the controller; and wherein the second air pump supplies the second pressurized air at the second pressure to the second cartridge assembly in response to receiving the second control signal from the controller. In one or more embodiments, the first cartridge assembly includes: a container in which the first liquid is contained; and a diffuser cap connected to the container. In one or more embodiments, the method further includes: removably receiving the first cartridge assembly within the first receptacle of the chassis assembly of the diffuser; wherein removably receiving the first cartridge assembly within the first receptacle of the chassis assembly of the diffuser includes: engaging the diffuser cap with the first receptacle; and suspending the container from the diffuser cap and within the chassis assembly. In one or more embodiments, supplying, using the first air pump of the diffuser, the first pressurized air at the first pressure to the first cartridge assembly of the diffuser includes: supplying the first pressurized air from the first air pump to an internal pressure chamber of the diffuser cap. In one or more embodiments, diffusing, with the first pressurized air supplied by the first air pump, the first liquid contained in the first cartridge assembly includes: supplying the first pressurized air from the internal pressure chamber to an internal diffuser chamber of the diffuser cap; and supplying the first liquid from the first container to the internal diffuser chamber of the diffuser cap.

A diffuser has also been disclosed. The diffuser generally includes: a chassis assembly including first and second receptacles; first and second cartridge assemblies removably received within the first and second receptacles, respectively, of the chassis assembly, wherein the first and second cartridge assemblies contain first and second liquids, respectively; a first air pump adapted to supply first pressurized air at a first pressure to the first cartridge assembly, wherein the first pressurized air supplied by the first air pump diffuses the first liquid contained in the first cartridge assembly; and a second air pump adapted to supply second pressurized air at a second pressure to the second cartridge assembly, wherein the second pressurized air supplied by the second air pump diffuses the second liquid contained in the second cartridge assembly. In one or more embodiments, the first pressure at which the first pressurized air is supplied to the first cartridge assembly by the first air pump is different from the second pressure at which the second pressurized air is supplied to the second cartridge assembly by the second air pump. In one or more embodiments, the diffuser further includes: a controller adapted to send first and second control signals to the first and second air pumps, respectively; wherein the first air pump is adapted to supply the first pressurized air at the first pressure to the first cartridge assembly in response to receiving the first control signal from the controller; and wherein the second air pump is adapted to supply the second pressurized air at the second pressure to the second cartridge assembly in response to receiving the second control signal from the controller. In one or more embodiments, the first cartridge assembly includes: a container in which the first liquid is contained; and a diffuser cap connected to the container. In one or more embodiments, the diffuser cap is engaged with the first receptacle; and the container is suspended from the diffuser cap within the chassis assembly. In one or more embodiments, the diffuser cap defines and internal pressure chamber; and the first air pump is adapted to supply the first pressurized air at the first pressure to the first cartridge assembly by supplying the first pressurized air to the internal pressure chamber. In one or more embodiments, the diffuser cap further defines and internal diffuser chamber; and, to diffuse the first liquid contained in the first cartridge assembly with the first pressurized air supplied by the first air pump: the internal pressure chamber is adapted to supply the first pressurized air to the internal diffuser chamber; and the first container is adapted to supply the first liquid to the internal diffuser chamber.

An apparatus has also been disclosed. The apparatus generally includes: a non-transitory computer readable medium; and a plurality of instructions stored on the non-transitory computer readable medium and executable by one or more processors, wherein, when the instructions are executed by the one or more processors, the following steps are executed: supplying, using a first air pump of a diffuser, first pressurized air at a first pressure to a first cartridge assembly of the diffuser, said first cartridge assembly being removably received within a first receptacle of a chassis assembly of the diffuser; diffusing, with the first pressurized air supplied by the first air pump, a first liquid contained in the first cartridge assembly; supplying, using a second air pump of the diffuser, second pressurized air at a second pressure to a second cartridge assembly of the diffuser, said second cartridge assembly being removably received within a second receptacle of the chassis assembly of the diffuser; and diffusing, with the second pressurized air supplied by the second air pump, a second liquid contained in the second cartridge assembly. In one or more embodiments, the first pressure at which the first pressurized air is supplied to the first cartridge assembly of the diffuser by the first air pump is different from the second pressure at which the second pressurized air is supplied to the second cartridge assembly of the diffuser by the second air pump. In one or more embodiments, when the instructions are executed by the one or more processors, the following step is also executed: receiving, from a controller, first and second control signals at the first and second air pumps, respectively; wherein the first air pump supplies the first pressurized air at the first pressure to the first cartridge assembly in response to receiving the first control signal from the controller; and wherein the second air pump supplies the second pressurized air at the second pressure to the second cartridge assembly in response to receiving the second control signal from the controller. In one or more embodiments, the first cartridge assembly includes: a container in which the first liquid is contained; and a diffuser cap connected to the container. In one or more embodiments, when the instructions are executed by the one or more processors, the following step is also executed: removably receiving the first cartridge assembly within the first receptacle of the chassis assembly of the diffuser; wherein removably receiving the first cartridge assembly within the first receptacle of the chassis assembly of the diffuser includes: engaging the diffuser cap with the first receptacle; and suspending the container from the diffuser cap and within the chassis assembly. In one or more embodiments, supplying, using the first air pump of the diffuser, the first pressurized air at the first pressure to the first cartridge assembly of the diffuser includes: supplying the first pressurized air from the first air pump to an internal pressure chamber of the diffuser cap. In one or more embodiments, diffusing, with the first pressurized air supplied by the first air pump, the first liquid contained in the first cartridge assembly includes: supplying the first pressurized air from the internal pressure chamber to an internal diffuser chamber of the diffuser cap; and supplying the first liquid from the first container to the internal diffuser chamber of the diffuser cap.

It is understood that variations may be made in the foregoing without departing from the scope of the present disclosure.

In one or more embodiments, the elements and teachings of the various embodiments may be combined in whole or in part in some or all of the embodiments. In addition, one or more of the elements and teachings of the various embodiments may be omitted, at least in part, and/or combined, at least in part, with one or more of the other elements and teachings of the various embodiments.

Any spatial references, such as, for example, "upper," "lower," "above," "below," "between," "bottom," "vertical," "horizontal," "angular," "upwards," "downwards," "side-to-side," "left-to-right," "right-to-left," "top-to-bottom," "bottom-to-top," "top," "bottom," "bottom-up," "top-down," etc., are for the purpose of illustration only and do not limit the specific orientation or location of the structure described above.

In one or more embodiments, while different steps, processes, and procedures are described as appearing as distinct acts, one or more of the steps, one or more of the processes, and/or one or more of the procedures may also be performed in different orders, simultaneously and/or sequentially. In one or more embodiments, the steps, processes, and/or procedures may be merged into one or more steps, processes and/or procedures.

In one or more embodiments, one or more of the operational steps in each embodiment may be omitted. Moreover, in some instances, some features of the present disclosure may be employed without a corresponding use of the other features. Moreover, one or more of the above-described embodiments and/or variations may be combined in whole or in part with any one or more of the other above-described embodiments and/or variations.

Although several embodiments have been described in detail above, the embodiments described are illustrative only and are not limiting, and those skilled in the art will readily appreciate that many other modifications, changes and/or substitutions are possible in the embodiments without materially departing from the novel teachings and advantages of the present disclosure. Accordingly, all such modifications, changes, and/or substitutions are intended to be included within the scope of this disclosure as defined in the following claims. In the claims, any means-plus-function clauses are intended to cover the structures described herein as performing the recited function and not only structural equivalents, but also equivalent structures. Moreover, it is the express intention of the applicant not to invoke 35 U.S.C. § 112(f) for any limitations of any of the claims herein, except for those in which the claim expressly uses the word "means" together with an associated function.

What is claimed is:

1. A method, comprising:
supplying, using a first air pump of a diffuser, first pressurized air at a first pressure to a first cartridge assembly of the diffuser,
wherein said first cartridge assembly is removably received, via a first opening, within a first receptacle of a chassis assembly of the diffuser so that the first cartridge assembly extends within both the first receptacle and the first opening, the first opening being:
aligned with the first receptacle; and
formed through an outside surface of the diffuser, the outside surface being defined by a cover of the chassis assembly,
wherein said first cartridge assembly comprises:
a first container in which a first liquid is contained; and
a first diffuser cap connected to the first container, the first diffuser cap defining a first internal pressure chamber,
and
wherein supplying, using the first air pump of the diffuser, the first pressurized air at the first pressure to the first cartridge assembly of the diffuser comprises:
supplying the first pressurized air from the first air pump to the first internal pressure chamber of the first diffuser cap;
diffusing, with the first pressurized air supplied by the first air pump, the first liquid contained in the first cartridge assembly,
wherein the first diffuser cap further defines a first internal diffuser chamber,
wherein the first internal pressure chamber is horizontally spaced apart from, and at least partially horizontally in line with, the first internal diffuser chamber, wherein the first internal pressure chamber is vertically spaced apart from, and horizontally spaced apart from, the first container in which the first liquid is contained, and wherein diffusing, with the first pressurized air supplied by the first air pump, the first liquid contained in the first cartridge assembly comprises:

supplying the first pressurized air from the first internal pressure chamber to the first internal diffuser chamber of the first diffuser cap via a first horizontally-extending internal passageway; and supplying the first liquid from the first container to the first internal diffuser chamber of the first diffuser cap;

supplying, using a second air pump of the diffuser, second pressurized air at a second pressure to a second cartridge assembly of the diffuser, wherein said second cartridge assembly is spaced apart from the first cartridge assembly;

wherein said second cartridge assembly is removably received, via a second opening, within a second receptacle of the chassis assembly of the diffuser so that the second cartridge assembly extends within both the second receptacle and the second opening, the second opening being:

aligned with the second receptacle; and formed through the outside surface of the diffuser, wherein said second receptacle is spaced apart from the first receptacle;

wherein said second cartridge assembly comprises:

a second container in which a second liquid is contained; and a second diffuser cap connected to the second container, the second diffuser cap defining a second internal pressure chamber and wherein supplying, using the second air pump of the diffuser, the second pressurized air at the second pressure to the second cartridge assembly of the diffuser comprises:

supplying the second pressurized air from the second air pump to the second internal pressure chamber of the second diffuser cap;

diffusing, with the second pressurized air supplied by the second air pump, the second liquid contained in the second cartridge assembly, wherein the second diffuser cap further defines a second internal diffuser chamber, wherein the second internal pressure chamber is horizontally spaced apart from, and at least partially horizontally in line with, the second internal diffuser chamber, wherein the second internal pressure chamber is vertically spaced apart from, and horizontally spaced apart from, the second container in which the second liquid is contained, and wherein diffusing, with the second pressurized air supplied by the second air pump, the second liquid contained in the second cartridge assembly comprises:

supplying the second pressurized air from the second internal pressure chamber to the second internal diffuser chamber of the second diffuser cap via a second horizontally-extending internal passageway; and supplying the second liquid from the second container to the second internal diffuser chamber of the second diffuser cap;

removably receiving the first cartridge assembly, via the first opening, within the first receptacle of the chassis assembly of the diffuser; and removably receiving the second cartridge assembly, via the second opening, within the second receptacle of the chassis assembly of the diffuser;

wherein removably receiving the first cartridge assembly, via the first opening, within the first receptacle of the chassis assembly of the diffuser comprises:

engaging the first diffuser cap with the first receptacle so that:

a first seal is at least partially vertically in line with, and is sealingly engaged vertically between, a first fitting and at least a portion of the first internal pressure chamber, thereby fluidically coupling a first conduit with the at least a portion of the first internal pressure chamber, said first conduit being fluidically coupled, in turn, with the first air pump; and the first diffuser cap extends within the first opening; and suspending the first container from the first diffuser cap and within the chassis assembly so that the first container extends within the first receptacle, wherein removably receiving the second cartridge assembly, via the second opening, within the second receptacle of the chassis assembly of the diffuser comprises:

engaging the second diffuser cap with the second receptacle so that:

a second seal is at least partially vertically in line with, and is sealingly engaged vertically between, a second fitting and at least a portion of the second internal pressure chamber, thereby fluidically coupling a second conduit with the at least a portion of the second internal pressure chamber, said second conduit being fluidically coupled, in turn, with the second air pump; and the second diffuser cap extends within the second opening; and suspending the second container from the second diffuser cap and within the chassis assembly so that the second container extends within the second receptacle;

wherein the first cartridge assembly further includes a first handle pivotably connected to the first diffuser cap and adapted to facilitate the removable receipt of the first cartridge assembly within the first opening and within the first receptacle of the chassis assembly of the diffuser;

wherein the second cartridge assembly further includes a second handle pivotably connected to the second diffuser cap and adapted to facilitate the removable receipt of the second cartridge assembly within the second opening and within the second receptacle of the chassis assembly of the diffuser;

wherein the diffuser is cylindrical;

wherein the first and second cartridge assemblies are:

spaced apart a first radial distance from a longitudinal axis extending through the center of the diffuser; and equally distributed circumferentially about the longitudinal axis at the first radial distance;

and wherein the first and second air pumps are:

spaced apart a second radial distance from the longitudinal axis, the second radial distance being different from the first radial distance; and circumferentially offset from the first and second cartridge assemblies, respectively, at the second radial distance.

2. The method of claim 1, wherein the first pressure at which the first pressurized air is supplied to the first cartridge assembly of the diffuser by the first air pump is different from the second pressure at which the second pressurized air is supplied to the second cartridge assembly of the diffuser by the second air pump.

3. The method of claim 1, further comprising:
receiving, from a controller, first and second control signals at the first and second air pumps, respectively;
wherein the first air pump supplies the first pressurized air at the first pressure to the first cartridge assembly in response to receiving the first control signal from the controller; and
wherein the second air pump supplies the second pressurized air at the second pressure to the second cartridge assembly in response to receiving the second control signal from the controller.

4. The method of claim 1, wherein:
the cover of the chassis assembly is a top cover; and
the outside surface of the diffuser defined by the top cover is an outside top surface of the diffuser.

5. A diffuser, comprising:
a chassis assembly, comprising:
first and second receptacles, the first and second receptacles being spaced apart from one another; and
a cover defining an outside surface of the diffuser, the cover including first and second openings formed through the outside surface and aligned with the first and second receptacles, respectively;
first and second cartridge assemblies removably received within the first and second receptacles, respectively, of the chassis assembly, the first and second cartridge assemblies being spaced apart from one another,
wherein the first and second cartridge assemblies contain first and second liquids, respectively;
wherein the first cartridge assembly is removably received, via the first opening, within the first receptacle of the chassis assembly so that the first cartridge assembly extends within both the first receptacle and the first opening, the first cartridge assembly comprising:
a first container in which the first liquid is contained; and
a first diffuser cap connected to the first container, the first diffuser cap defining a first internal pressure chamber;
wherein a first air pump is adapted to supply the first pressurized air at the first pressure to the first cartridge assembly by supplying the first pressurized air to the first internal pressure chamber of the first diffuser cap;
wherein the second cartridge assembly is removably received, via the second opening, within the second receptacle of the chassis assembly so that the second cartridge assembly extends within both the second receptacle and the second opening, the second cartridge assembly comprising:
a second container in which the second liquid is contained; and
a second diffuser cap connected to the second container, the second diffuser cap defining a second internal pressure chamber:
and
wherein a second air pump is adapted to supply the second pressurized air at the second pressure to the second cartridge assembly by supplying the second pressurized air to the second internal pressure chamber of the second diffuser cap;
the first air pump, which is adapted to supply first pressurized air at a first pressure to the first cartridge assembly,
wherein the first pressurized air supplied by the first air pump diffuses the first liquid contained in the first cartridge assembly;
wherein the first diffuser cap further defines a first internal diffuser chamber;
wherein the first internal pressure chamber is horizontally spaced apart from, and at least partially horizontally in line with, the first internal diffuser chamber;
wherein the first internal pressure chamber is vertically spaced apart from, and horizontally spaced apart from, the first container in which the first liquid is contained; and
wherein, to diffuse the first liquid contained in the first cartridge assembly with the first pressurized air supplied by the first air pump:
the first internal pressure chamber is adapted to supply the first pressurized air to the first internal diffuser chamber via a first horizontally-extending internal passageway; and
the first container is adapted to supply the first liquid to the first internal diffuser chamber;
and
the second air pump, which is adapted to supply second pressurized air at a second pressure to the second cartridge assembly,
wherein the second pressurized air supplied by the second air pump diffuses the second liquid contained in the second cartridge assembly;
wherein the second diffuser cap further defines a second internal diffuser chamber;
wherein the second internal pressure chamber is horizontally spaced apart from, and at least partially horizontally in line with, the second internal diffuser chamber;
wherein the second internal pressure chamber is vertically spaced apart from, and horizontally spaced apart from, the second container in which the second liquid is contained; and
wherein, to diffuse the second liquid contained in the second cartridge assembly with the second pressurized air supplied by the second air pump:
the second internal pressure chamber is adapted to supply the second pressurized air to the second internal diffuser chamber via a second horizontally-extending internal passageway; and
the second container is adapted to supply the second liquid to the second internal diffuser chamber;
wherein:
a first seal is at least partially vertically in line with, and is sealingly engaged vertically between, a first fitting and at least a portion of the first internal pressure chamber, thereby fluidically coupling a first conduit with the at least a portion of the first internal pressure chamber, said first conduit being fluidically coupled, in turn, with the first air pump;
the first diffuser cap is engaged with the first receptacle and extends within the first opening; and
the first container is suspended from the first diffuser cap within the chassis assembly and extends within the first receptacle;

wherein:
a second seal is at least partially vertically in line with, and is sealingly engaged vertically between, a second fitting and at least a portion of the second internal pressure chamber, thereby fluidically coupling a second conduit with the at least a portion of the second internal pressure chamber, said second conduit being fluidically coupled, in turn, with the second air pump;
the second diffuser cap is engaged with the second receptacle and extends within the second opening; and
the second container is suspended from the second diffuser cap within the chassis assembly and extends within the second receptacle;
wherein the first cartridge assembly further includes a first handle pivotably connected to the first diffuser cap and adapted to facilitate the removable receipt of the first cartridge assembly within the first opening and within the first receptacle of the chassis assembly of the diffuser;
wherein the second cartridge assembly further includes a second handle pivotably connected to the second diffuser cap and adapted to facilitate the removable receipt of the second cartridge assembly within the second opening and within the second receptacle of the chassis assembly of the diffuser;
wherein the diffuser is cylindrical;
wherein the first and second cartridge assemblies are:
spaced apart a first radial distance from a longitudinal axis extending through the center of the diffuser; and
equally distributed circumferentially about the longitudinal axis at the first radial distance;
and
wherein the first and second air pumps are:
spaced apart a second radial distance from the longitudinal axis, the second radial distance being different from the first radial distance; and
circumferentially offset from the first and second cartridge assemblies, respectively, at the second radial distance.

6. The diffuser of claim 5, wherein the first pressure at which the first pressurized air is supplied to the first cartridge assembly by the first air pump is different from the second pressure at which the second pressurized air is supplied to the second cartridge assembly by the second air pump.

7. The diffuser of claim 5, further comprising:
a controller adapted to send first and second control signals to the first and second air pumps, respectively;
wherein the first air pump is adapted to supply the first pressurized air at the first pressure to the first cartridge assembly in response to receiving the first control signal from the controller; and
wherein the second air pump is adapted to supply the second pressurized air at the second pressure to the second cartridge assembly in response to receiving the second control signal from the controller.

8. The diffuser of claim 5, wherein:
the cover of the chassis assembly is a top cover; and
the outside surface of the diffuser defined by the top cover is an outside top surface of the diffuser.

* * * * *